US00PP29881P2

(12) United States Plant Patent
Zaiger et al.

(10) Patent No.: US PP29,881 P2
(45) Date of Patent: Nov. 27, 2018

(54) INTERSPECIFIC TREE NAMED 'SUNSET PLAPPLE'

(50) Latin Name: ***Interspecific Prunus* species**
Varietal Denomination: Sunset Plapple

(71) Applicants: Gary Neil Zaiger, Modesto, CA (US); Leith Marie Gardner, Modesto, CA (US); Grant Gene Zaiger, Modesto, CA (US)

(72) Inventors: Gary Neil Zaiger, Modesto, CA (US); Leith Marie Gardner, Modesto, CA (US); Grant Gene Zaiger, Modesto, CA (US)

( * ) Notice: Subject to any disclaimer, the term of this patent is extended or adjusted under 35 U.S.C. 154(b) by 0 days.

(21) Appl. No.: 15/732,678

(22) Filed: Dec. 14, 2017

(51) Int. Cl.
*A01H 5/08* (2018.01)

(52) U.S. Cl.
USPC ..... Plt./180
CPC ..... *A01H 5/08* (2013.01)

(58) Field of Classification Search
USPC ..... Plt./180
CPC ..... A01H 5/0837
See application file for complete search history.

*Primary Examiner* — Kent L Bell

(57) ABSTRACT

A new and distinct variety of interspecific tree. The following features of the tree and its fruit are characterized with the tree budded on 'Nemaguard' Rootstock (non-patented), grown on Handford sandy loam soil with Storie Index rating 95, in USDA Hardiness Zone 9, near Modesto, Calif., with standard commercial fruit growing practices, such as pruning, thinning, spraying, irrigation and fertilization. Its novelty consist of the following combination of desirable features:

1. Tree having a vigorous, upright growth habit.
2. Tree being a regular and productive bearer of medium to large size fruit.
3. Fruit having firm, white flesh with very good flavor and eating quality.
4. Fruit with an attractive mottled red skin color.
5. Fruit with good storage and shipping quality.

1 Drawing Sheet

Botanical designation: Interspecific *Prunus* species.
Variety denomination: 'Sunset Plapple'.

BACKGROUND OF THE VARIETY

Field of the Invention

In the field of plant genetics, we conduct an extensive and continuing plant-breeding program including the organization and asexual reproduction of orchard trees, and of which plums, peaches, nectarines, apricots, cherries, almonds and interspecifics are exemplary. It was against this background of our activities that the present variety of interspecific tree was originated and asexually reproduced by us in our experimental orchard located near Modesto, Stanislaus County, Calif.

PRIOR VARIETIES

Among the existing varieties of interspecific trees, which are known to us, and mentioned herein, 'Black Kat' Interspecific (U.S. Plant Pat. No. 13,134), 'Flavor Grenade' Interspecific (U.S. Plant Pat. No. 12,097) and the proprietary non-patented interspecific seedling selections '20M57', '54ZD402', '67Z130', '20Z98', and '45GK282'.

STATEMENT REGARDING FEDERALLY SPONSORED RESEARCH AND DEVELOPMENT

Not applicable.

ORIGIN OF THE VARIETY

The new and distinct variety of interspecific tree was developed by us in our experimental orchard located near Modesto, Calif. from a first generation cross between our proprietary non-patented interspecific seedlings with the field identification numbers '20M57' and '54ZD402'. The seed parent '20M57' is a first generation cross from our proprietary non-patented interspecific seedling selections '67Z130' and '20Z98'. The pollen parent '54ZD402' originated as a first generation cross between 'Flavor Grenade' Interspecific (U.S. Plant Pat. No. 12,097) and our proprietary non-patented interspecific seedling selection '45GK282'. A large number of these first generation seedlings were planted and maintained on their own root system and under close and careful observation we recognized the desirable fruit and tree characteristics of the present variety and selected it in 2008 for additional asexual propagation and commercialization.

ASEXUAL REPRODUCTION OF THE VARIETY

In 2008 asexual reproduction of the new and distinct variety of interspecific tree was by budding to 'Nemaguard' Rootstock (non-patented), as performed by us in our experimental orchard located near Modesto, Calif., and shows that reproductions run true to the original tree and all characteristics of the tree and its fruit are established and transmitted through succeeding asexual propagations.

SUMMARY OF THE NEW VARIETY

The present new and distinct variety of interspecific tree, which consists of crosses between *Prunus salicina* and

*Prunus armeniaca* has vigorous, upright growth and is a regular and productive bearer of medium to large size fruit with a mottled red skin color. The fruit is further characterized by its firm, white flesh and very good flavor and eating quality. In comparison to its proprietary non-patented seed parent (20M57) the fruit of the new variety has white flesh compared to yellow and is approximately 12 days earlier in maturity. In comparison to its proprietary non-patented pollen parent (54ZD402) the fruit of the new variety has white flesh compared to yellow and is approximately 25 days earlier in maturity. In comparison to the commercial variety 'Black Kat' Interspecific (U.S. Plant Pat. No. 13,134) the fruit of the new variety has mottled red skin compared to blackish-blue skin and is approximately 1 week later in maturity.

DESCRIPTION OF THE PHOTOGRAPH

The accompanying color photographic illustration shows typical specimens of the foliage and fruit of the present new interspecific variety. The illustration shows the upper and lower surface of the leaves, an exterior and sectional view of a single fruit divided in its suture plane to show flesh color, pit cavity and the stone remaining in place. The photographic illustration was taken shortly after being picked (shipping ripe) from a 9 year old tree and the colors are as nearly true as is reasonably possible in a color representation of this type.

DESCRIPTION OF THE VARIETY

The following is a detailed botanical description of the new variety of interspecific tree, its flowers, foliage and fruit, as based on observations of 9 year old specimens grown near Modesto, Calif., with color in accordance with Munsell Book of Color published in 1958.

Tree:

*Size*.—Large, pruned to 3 to 3.5 meters in height and width for economical harvesting of fruit. Varies with different cultural practices.

*Vigor*.—Vigorous, tree growth of 1.5 to 2 meters the first growing season. Varies with cultural practices, soil type, fertility and climatic conditions.

*Form*.—Upright growth, usually pruned to vase shape.

*Branching habit*.—Upright, crotch angle approximately 35°, increases with heavy crop load.

*Productivity*.—Productive, thinning and spacing of fruit necessary for desired market size fruit. Number of fruit set varies with climatic conditions during blooming period.

*Bearer*.—Regular, adequate fruit set 7 consecutive years. No alternate bearing observed.

*Fertility*.—Self-sterile, pollinator required.

*Density*.—Medium dense, usually pruned to vase shape to increase air movement and sunlight to enhance fruit color and health of fruit spurs.

*Hardiness*.—Hardy in all stone fruit growing areas of California. Tree grown in USDA Hardiness Zone 9. Winter chilling requirement approximately. 650 hours at or below 45° F.

Trunk:

*Size*.—Large. Average circumference 58.4 cm at 25.4 cm above ground on a 9 year old tree.

*Stocky*.—Medium stocky.

*Texture*.—Medium shaggy, roughness increases with age of tree.

*Color*.—7.5YR 2/2.

Branches:

*Size*.—Medium. Average circumference 19.1 cm at 1.2 meters above ground. Crotch angle approximately 35°, increases with heavy crop load.

*Surface texture*.—New growth relatively smooth. Mature growth medium rough, roughness increases with age.

*Lenticels*.—Average number 28 in 25.8 square cm area. Average length 6.3 mm. Average width 2.5 mm. Color varies from 7.5YR 4/6 to 5YR 5/12.

*Color*.—New growth varies from 2.5GY 6/8 to 2.5GY 5/8. Mature growth varies from 7.5YR 5/4 to 7.5YR 3/4, varies with age of growth.

Leaves:

*Size*.—Medium. Average length 90.9 mm. Average width 39.5 mm.

*Form*.—Oblanceolate.

*Apex*.—Acuminate.

*Base*.—Cuneate.

*Margin*.—Serrate.

*Thickness*.—Medium.

*Surface texture*.—Upper surface relatively smooth, slight indentations over midrib and leaf veins. Lower surface relatively smooth, except for small ridges created by midrib and pinnate venation. Both upper and lower surfaces glabrous.

*Petiole*.—Average length 19.3 mm. Average width 1.3 mm. Longitudinally grooved. Surface — glabrous. Color 5GY 7/4.

*Glands*.—Type — globose. Size — small. Average length 1.0 mm. Average diameter 0.5 mm. Average number 2, varies from 1 to 3. Located primarily on the base of the leaf blade and upper portion of petiole. Color varies from 5GY 6/6 to 7.5GY 6/6.

*Stipules*.—None present at time of measurement.

*Color*.—Upper surface 5GY 3/4. Lower surface 5GY 4/4. Midvein color 2.5GY 7/4.

Flower buds:

*Size*.—Small. Average length 7.0 mm. Average diameter 4.3 mm.

*Hardiness*.—Hardy with respect to California winters.

*Density*.—Medium.

*Form*.—Conical, becoming elongated just before opening.

*Pedicel*.—Average length 7.3 mm. Average width 0.8 mm. Surface — glabrous. Color varies from 2.5GY 7/6 to 5GY 7/8.

*Color*.—N 9.5/(white).

*Number of buds per spur*.—Average number 10, varies from 6 to 14.

Flowers:

*Blooming period*.—Date of First Bloom Mar. 1, 2017. Date of Petal Fall Mar. 11, 2017, varies slightly with climatic conditions.

*Size*.—Small to medium. Average height 7.5 mm. Average diameter 15.9 mm.

*Petals*.—Normally 5, alternately arranged to sepals. Size — small to medium. Average length 8.0 mm. Average width 6.4 mm. Petal apex — rounded. Petal base — truncate. Form — globose to elliptical. Margin — sinuate. Arrangement — free to very slightly overlapping. Both upper and lower surfaces glabrous. Color N 9.5/(white).

*Sepals*.—Normally 5, alternately arranged to petals. Size — small. Average length 2.7 mm. Average width 2.5 mm. Sepal apex — triangular to slightly rounded. Shape — triangular. Margin — entire. Both upper and lower surfaces glabrous. Color — upper surface varies from 5GY 6/6 to 5GY 6/8. Lower surface varies from 5GY 6/6 to 7.5GY 7/6.

*Stamens*.—Average number per flower 29. Average filament length 5.6 mm. On average, the stamens are above the height of the petals. Filament color N 9.5/(white). Anther color varies from 7.5GY 8/8 to 10Y 8.5/8.

*Pollen*.—Self sterile, pollinator required. Color varies from 5Y 7/10 to 5Y 7/8.

*Pistil*.—Number — normally 1. Average length 6.2 mm. Position of stigma an average of 1.0 mm below anthers. Surface — glabrous. Color varies from 10Y 8/6 to 2.5GY 8/6.

*Fragrance*.—Heavy aroma.

*Flower color*.—N 9.5/(white).

*Pedicel*.—Average length 7.6 mm. Average width 0.9 mm. Color varies from 2.5GY 6/6 to 5GY 7/6.

*Number flowers per flower bud*.—Average 3, varies from 1 to 3.

Fruit:

*Maturity when described*.—Firm ripe and ready for consumption.

*Date of first picking*.—Sep. 11, 2017.

*Date of last picking*.—Sep. 21, 2017, varies slightly with climatic conditions.

*Size*.—Medium to large. Average diameter axially 64.4 mm. Average transversely in suture plane 63.4 mm. Average weight 168.0 grams, varies slightly with fertility of the soil, amount of thinning and climatic conditions.

*Form*.—Globose.

*Suture*.—Lipped.

*Ventral surface*.—Lipped.

*Apex*.—Rounded.

*Base*.—Flat.

*Stem cavity*.—Rounded. Average depth 5.3 mm. Average diameter 5.0 mm.

Stem:

*Size*.—Medium. Average length 13.0 mm. Average diameter 2.3 mm.

*Color*.—Varies from 7.5YR 4/6 to 7.5YR 3/6.

Flesh:

*Ripens*.—Evenly.

*Texture*.—Firm, meaty.

*Fibers*.—Few, small, tender.

*Firmness*.—Firm, comparable to other commercial interspecific varieties.

*Aroma*.—Moderate.

*Amydgalin*.—Undetected.

*Eating quality*.—Very good.

*Flavor*.—Very good, good balance between acid and sugar.

*Juice*.—Heavy amount, enhances flavor.

*Acidity*.—Not available.

*Brix*.—Average Brix 22.0°, varies slightly with amount of fruit per tree and climatic conditions.

*Color*.—Varies from 2.5Y 8.5/2 to 5Y 8.5/4.

*Pit cavity*.—Average length 28.4 mm. Average width 18.2 mm. Average depth 9.7 mm. Color varies from 2.5Y 7/6 to 2.5Y 6/6.

Skin:

*Thickness*.—Medium.

*Surface*.—Smooth.

*Bloom*.—Moderate amount, complete coverage.

*Tendency to crack*.—None.

*Color*.—Ground color varies from 2.5Y 8.5/6 to 2.5Y 8/4. Overspread with 5R 3/8 to 5R 4/10. Very small, randomly spaced areas of ground color exposed to give a speckled and mottled pattern to the red skin.

*Tenacity*.—Tenacious to the flesh.

*Astringency*.—Slight to none.

Stone:

*Type*.—Clingstone, medium adherence to the flesh.

*Size*.—Medium to large. Average length 27.4 mm. Average width 17.2 mm. Average thickness 8.7 mm.

*Form*.—Obovoid.

*Base*.—Flat.

*Apex*.—Pointed. Average length 1.8 mm.

*Surface*.—Slightly pitted throughout. One shallow groove on each side of suture extending from base to apex.

*Sides*.—Unequal, one side extending further from suture plane.

*Ridges*.—Very narrow, small ridge near groove on each side of suture, extends from base to apex.

*Tendency to split*.—None.

*Color*.—Varies from 7.5YR 5/6 to 7.5YR 6/6, when dry.

Kernel:

*Size*.—Medium. Average length 17.6 mm. Average width 9.3 mm. Average depth 4.8 mm.

*Form*.—Ovate.

*Viability*.—Viable, complete embryo development.

*Skin color*.—Varies from 10YR 5/8 to 7.5YR 5/8.

Use:

*Dessert*.—Market — local and long distance.

Keeping quality: Good, held firm in cold storage for 3 weeks at 38° to 42° F. without internal breakdown of flesh or appreciable loss of eating quality.

Shipping quality: Good, showed minimal skin scarring or flesh bruising during picking, packing and shipping trials.

Plant/fruit disease resistance/susceptibility: No specific testing for relative plant/fruit disease resistance/susceptibility has been designed. Under close observation during planting, growing and harvesting of fruit, under normal cultural and growing conditions near Modesto, Calif., no particular plant/fruit disease resistance or susceptibility has been observed. Any variety observed during indexing of plant characteristics with abnormal fungus, bacterial, virus or insect susceptibility is destroyed and eliminated from our breeding program. No atypical resistances/susceptibilities have been noted under normal cultural practices. The present new variety of interspecific tree, its flowers, foliage and fruit herein described may vary in slight detail due to climate, soil conditions and cultural practices under which the variety may be grown. The present description is that of the variety grown under the ecological conditions prevailing near Modesto, Calif.

The invention claimed is:

1. A new and distinct variety of interspecific tree, substantially as illustrated and described.

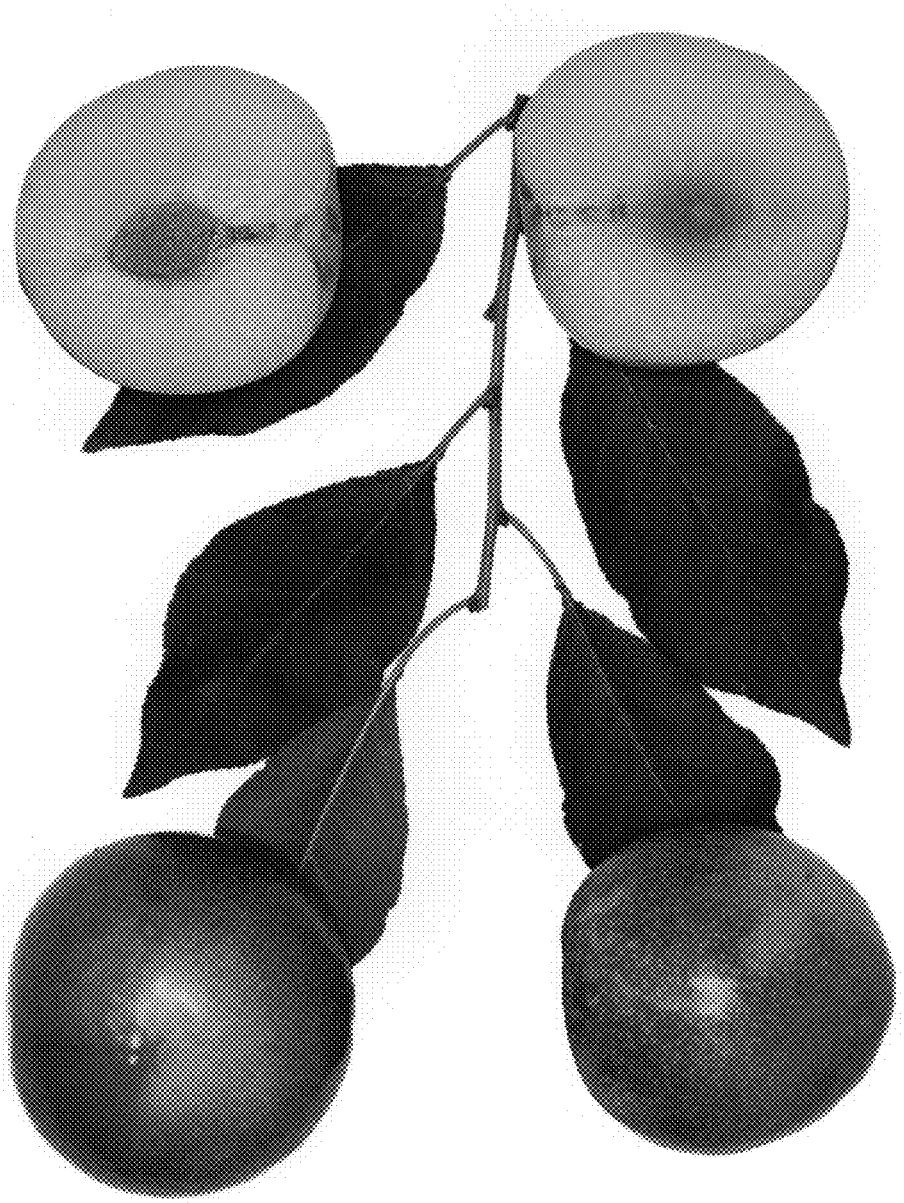

* * * * *